United States Patent [19]

Reddy

[11] 4,454,885

[45] Jun. 19, 1984

[54] ASSESSING ARTERIAL SYSTEMS

[75] Inventor: Daniel J. Reddy, Detroit, Mich.

[73] Assignee: Henry Ford Hospital, Detroit, Mich.

[21] Appl. No.: 275,854

[22] Filed: Jun. 22, 1981

[51] Int. Cl.³ .............................................. A61B 5/02
[52] U.S. Cl. ...................................... 128/707; 128/691
[58] Field of Search ...................... 128/25 B, 669, 670,
128/672, 691, 694, 707; 272/66, 73, 134, 135,
144, DIG. 4, DIG. 6

[56] References Cited

U.S. PATENT DOCUMENTS

| 3,395,698 | 10/1968 | Morehouse | 128/707 |
| 3,749,400 | 7/1973 | Stoffel | 272/134 |
| 4,206,764 | 6/1980 | Williams | 128/677 |
| 4,285,515 | 10/1981 | Gezari | 128/707 |

Primary Examiner—William E. Kamm
Assistant Examiner—Mitchell J. Shein
Attorney, Agent, or Firm—Barnes, Kisselle, Raisch, Choate, Whittemore & Hulbert

[57] ABSTRACT

A method and apparatus of assessing peripheral arterial systems comprising positioning a patient on an examining table in supine position with the legs of the patient flexed, positioning a treadle mechanism on the table so that the resiliently mounted foot pedals thereof are engaged by the feet of the patient, causing the patient to successively depress and release successive left and right foot pedals for a predetermined time or until claudication occurs, and thereafter making systolic pressure measurements on the legs of the patient.

2 Claims, 4 Drawing Figures

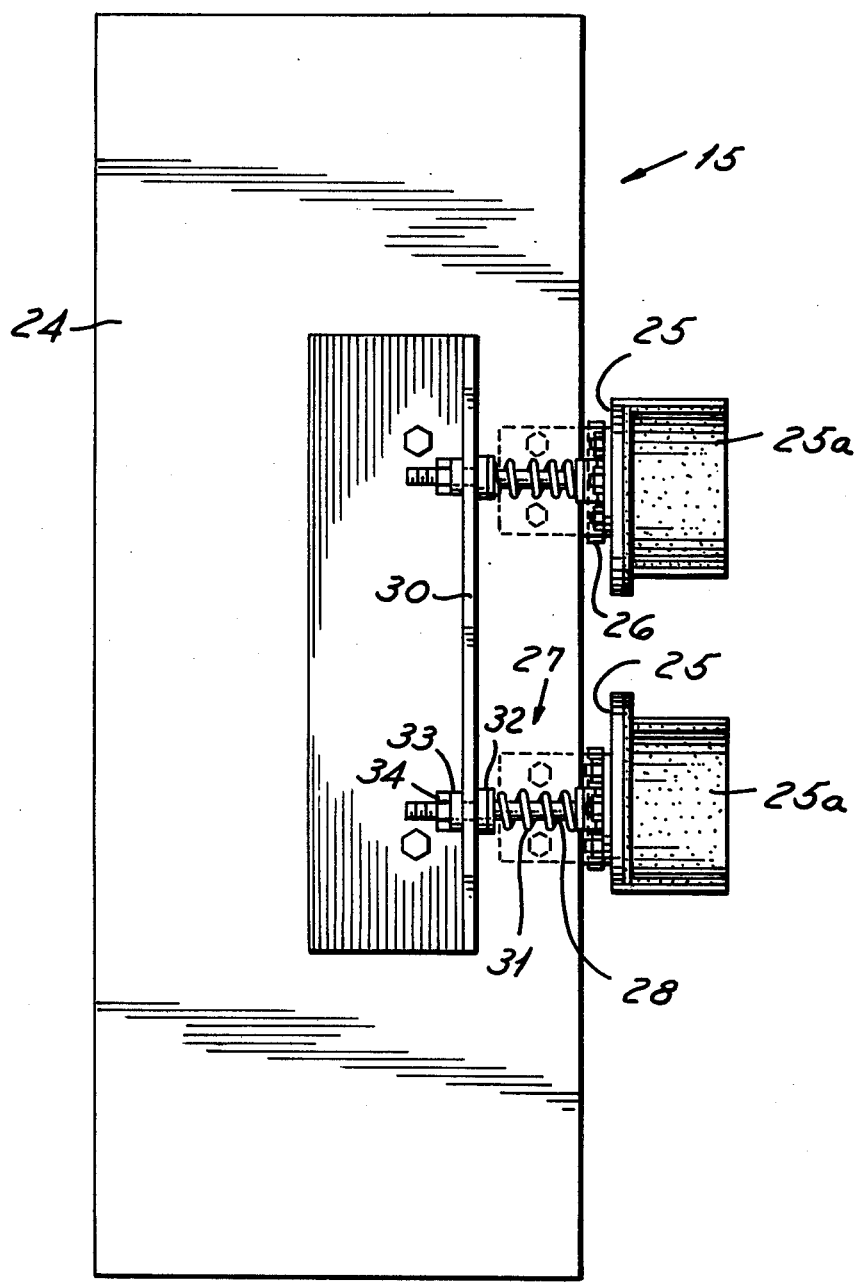

ASSESSING ARTERIAL SYSTEMS

This invention relates to assessing the arterial system of patients for determining arterial problems.

BACKGROUND AND SUMMARY OF THE INVENTION

The value of post-exercise doppler systolic pressure measurements to thoroughly assess the peripheral arterial system is well known. A number of exercise techniques are known. These include treadmill walking, post occlusive reactive hyperemia, ankle flexion maneuvers, toelifts, walking and climbing stairs. The most commonly used techniques are the constant-load treadmill and reactive hyperemia.

In the use of the constant-load treadmill technique some problems have been encountered. Principally, it has been found that a number of patients are unable to safely tolerate the treadmill exercise because of cardiac, pulmonary or neuromuscular conditions. The unilateral amputee, uncooperative or debilitated patients also present particular problems.

A few patients also have difficulty with the mile and one-half per hour speed and ten percent elevation of the treadmill. Another drawback is the time lag experienced from the cessation of exercise to placement of the patient on an examining table for the initial post-exercise blood pressure measurement. In some cases, as long as a minute and a half may elapse before the first post-exercise pressure can be obtained. This is attributed to the time necessary to assist these patients off the treadmill, obtain their cooperation in resuming the supine position and readjusting the equipment.

The present invention is directed to these problems of safety, cooperation, logistics and accuracy and utilizes a portable treadle mechanism for lower extremity exercise capable of being adapted to an examining table. More specifically, a patient is positioned on a examining table in supine position with the legs flexed and a treadle mechanism is positioned on the table so that the resiliently mounted foot pedals thereof are engaged by the feet of the patient. The patient is caused to successively depress and release successive left and right foot pedals for a predetermined period of time, or until claudication occurs, and thereafter systolic pressure measurements are made on the legs of the patient.

DESCRIPTION OF THE DRAWINGS

FIG. 4 is a plane view taken in the direction of the arrow 4 in FIG. 1.

DESCRIPTION

Figure 1:
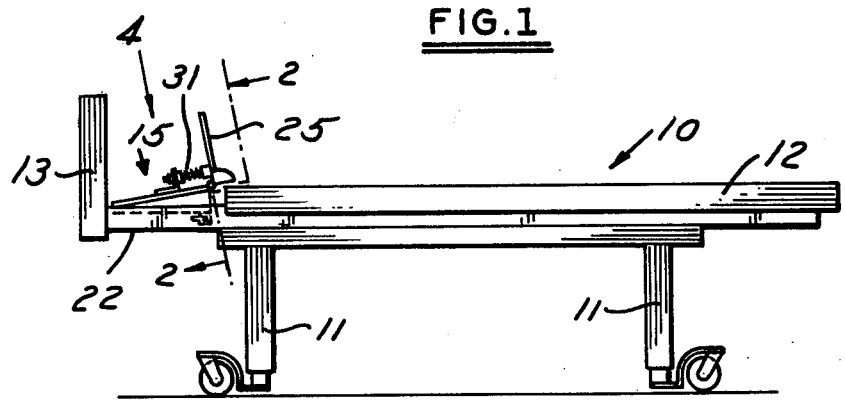
FIG. 1 is a side elevational view of an examining table embodying the invention.
Figure 2:
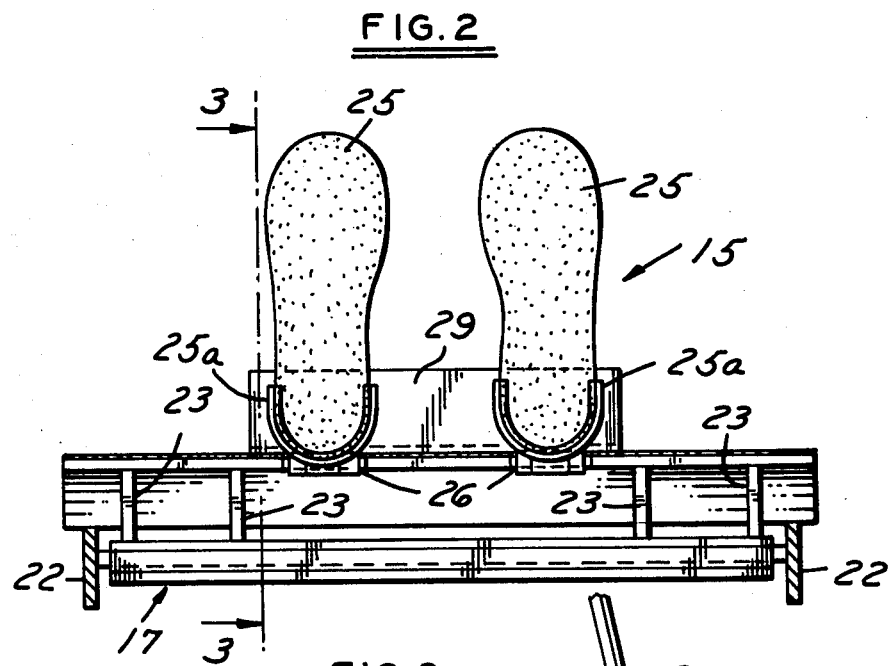
FIG. 2 is a sectional view on an enlarged scale taken along the line 2—2 in FIG. 1.
Figure 3:
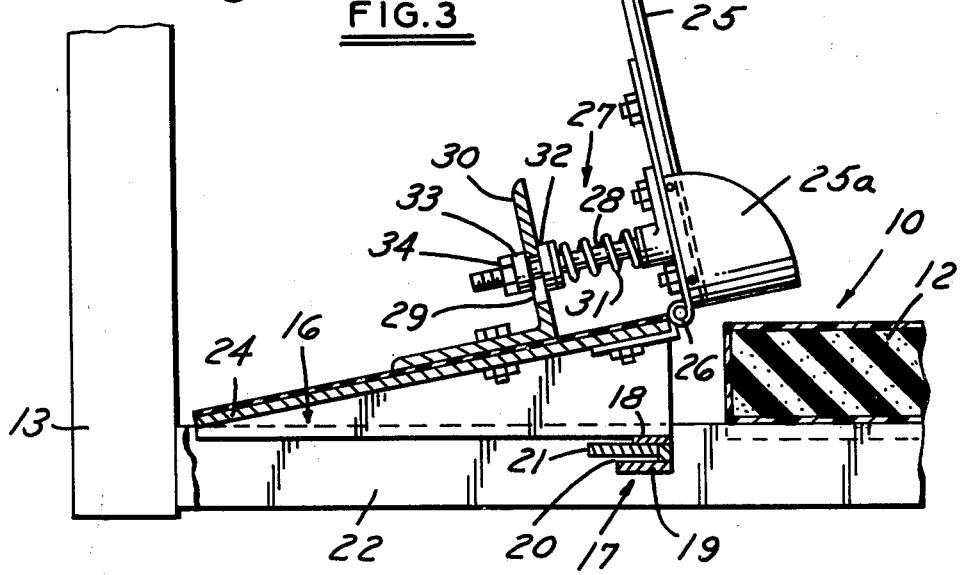
FIG. 3 is a sectional view taken along the line 3—3 in FIG. 2.

Referring to FIG. 1, the apparatus comprises a conventional examining table 10 having legs 11, a patient support pad 12 and a pivoted pad 13 at one end. A treadle mechanism 15 is removably mounted on the table 10 when pad 13 is pivoted to the position shown in FIG. 1.

Referring to FIGS. 1–4, the treadle mechanism 15 comprises a base 16 including a mounting bar 17 having spaced walls 18, 19 defining a slot 20 extending away from the patient for engaging the transverse bar 21 extending between longitudinal rails 22 of an examining table 10. The base further includes triangular-shaped vertical members 23 supporting an inclined top plate 24. A pair of foot pedals 25 with heel supports 25a are pivoted adjacent the heels thereof to the free edge of the plate by hinges 26. Each pedal 25 is resiliently urged toward the patient by spring means 27 including a shaft 28 fixed to the rear of each pedal 25 and extending through an elongated slot 29 in an upright wall 30 on the upper surface of the wall 24. A spring 31 is mounted on each shaft 28 and a low friction washer 32 of plastic or the like is interposed between the end of the spring 31 and the upright wall 30. A second low friction washer 33 of plastic is provided on the other side of the upright member 30 and a nut 34 is threaded on the shaft 28 to adjustably vary the tension on each pedal 25 as desired.

In practice, the treadle mechanism 15 is mounted on the cross rail 21 of the examining table so that the hinge axis of the pedals is substantially at the same elevation as the top surface of the pad 12 on the examining table 10.

Prior to exercise, resting ankle systolic pressures are obtained using 9 cm. standard pneumatic cuffs and a 9.8 mHz Doppler probe.

With the patient remaining in a supine position, the patient is caused to depress and release the spring-loaded foot pedals alternately, right, left, right, left. A metronome assists the patient in maintaining a rhythmic beat of preferably 88 depressions per minute. Thereby the spring tension necessary to depress the foot pedals and the rate of 88 depressions per minute is kept constant. The exercise is discontinued when the patient complains of claudication or completes an arbitrary ten minutes. With this treadle exercise a patient's exercise tolerance can be charted and followed to determined the progression of his disease. This also provides an objective pre-operative baseline for post-operative comparison and follow-up.

Based on a pilot study, it as been shown that while this treadle mechanism is less exercise than the standard treadmill as measured by the percentage of pressure drop and the recovery time, it does provide enough exercise to the legs to differentiate normal from abnormal peripheral arterial blood flow. The exercise can be performed by virtually all patients, and causes no cardiac or pulmonary complications. Arterial pressures can be obtained immediately after the exercise is stopped.

The design is relatively simple, compact and portable requiring much less space than the treadmill. The design is also inexpensive.

I claim:

1. A method of assessing peripheral arterial systems in the leg between the knee and the ankle comprising
    positioning a patient on an examining table in supine position with the legs flexed,
    positioning resiliently mounted pivoted foot pedals so that they are engaged by the feet of the patient when in the supine position with the legs flexed,
    causing the patient to successively depress and release successive left and right foot pedals,
    continuing said depressing and releasing for a predetermined time or until claudication occurs,
    and thereafter immediately making systolic pressure measurements on the legs of the patient between the knee and the ankle while the patient is in supine position on the examining table.

2. A method of assessing peripheral arterial systems in the leg between the knee and the ankle comprising positioning a patient on an examining table in supine position with the legs flexed, positioning a resiliently mounted pivoted foot pedal so that it is engaged by a foot of the patient when in supine position with the leg flexed, causing the patient to successively depress and release said foot pedal, continuing said depressing and releasing for a predetermined time or until claudication occurs, and thereafter immediately making systolic pressure measurements on the leg of the patient between the knee and the ankle while the patient is in supine position on the examining table.

* * * * *